US008271090B1

(12) United States Patent
Hartman et al.

(10) Patent No.: US 8,271,090 B1
(45) Date of Patent: Sep. 18, 2012

(54) APPARATUS AND METHODS FOR PROVIDING ELECTRICAL STIMULATION (75) Inventors: Eric C. Hartman, Lexington, KY (US); John D. Alton, Lexington, KY (US); Tarik S. Aweimrin, Lexington, KY (US)

(73) Assignee: Customkynetics, Inc., Versailles, KY (US)

( * ) Notice: Subject to any disclaimer, the term of this patent is extended or adjusted under 35 U.S.C. 154(b) by 142 days.

(21) Appl. No.: 12/826,073

(22) Filed: Jun. 29, 2010

Related U.S. Application Data (60) Provisional application No. 61/222,738, filed on Jul. 2, 2009.

(51) Int. Cl.
*A61N 1/00* (2006.01)
(52) U.S. Cl. .......................................................... 607/48
(58) Field of Classification Search .................... 606/32; 607/48, 40, 45, 30, 116, 118, 17, 72, 9
See application file for complete search history.

(56) References Cited

U.S. PATENT DOCUMENTS

| | | | |
|---|---|---|---|
| 4,712,558 A | 12/1987 | Kidd et al. | |
| 5,107,835 A | 4/1992 | Thomas | |
| 5,167,229 A | 12/1992 | Peckham et al. | |
| 5,562,707 A | 10/1996 | Prochazka et al. | |
| 5,601,617 A | 2/1997 | Loeb et al. | |
| 6,052,624 A | 4/2000 | Mann | |
| 6,728,577 B2 | 4/2004 | Minogue et al. | |
| 6,944,503 B2 | 9/2005 | Crowe et al. | |
| 7,162,305 B2 | 1/2007 | Tong et al. | |
| 7,519,427 B2 | 4/2009 | Sakagami et al. | |
| 7,613,518 B2 | 11/2009 | Qin et al. | |
| 2004/0167585 A1* | 8/2004 | Kovak et al. | 607/48 |
| 2005/0033377 A1 | 2/2005 | Milojevic et al. | |
| 2005/0137651 A1 | 6/2005 | Litvak et al. | |
| 2006/0106375 A1* | 5/2006 | Werneth et al. | 606/32 |
| 2009/0228068 A1* | 9/2009 | Buhlmann et al. | 607/48 |
| 2009/0248110 A1 | 10/2009 | Choi et al. | |
| 2010/0004715 A1 | 1/2010 | Fahey | |

FOREIGN PATENT DOCUMENTS

| | | |
|---|---|---|
| EP | 108341 | 5/1984 |
| EP | 587269 | 3/1994 |
| JP | 2000-245853 | 9/2000 |

OTHER PUBLICATIONS

"RT50 wireless stimulator", Restorative Therapies, http://www.restorative-therapies.com/rt50wirelessstimulators Posted Oct. 7, 2010, 3 Pages.
U.S. Appl. No. 12/250,018, filed Oct. 13, 2008 Eric C. Hartman.
U.S. Appl. No. 12/164,554, filed Jun. 30, 2008 Eric C. Hartman.
U.S. Appl. No. 11/483,786, filed Jul. 10, 2006 Eric C. Hartman.
510(k) Summary of Safety and Effectiveness in accordance with 21 CFR 807.92 May 23, 2005 6 Pages.
www.lgmedsupply.com/ntneelstandt.htlm NT2000 TENS Unit and Muscle Stimulator (NMES) Dec. 15, 2011 3 Pages.

* cited by examiner

*Primary Examiner* — George Manuel
*Assistant Examiner* — Robert N Wieland
(74) *Attorney, Agent, or Firm* — King & Schickli, PLLC (57) ABSTRACT

An apparatus is disclosed for providing electrical stimulation to a subject from a stimulation unit using a transmission line and a plurality of electrodes. The apparatus may include a plurality of discrete nodes, each adapted to connect to the transmission line for receiving the electrical stimulation and to connect with at least one pair of the plurality of electrodes. Related methods are also described.

39 Claims, 10 Drawing Sheets

APPARATUS AND METHODS FOR PROVIDING ELECTRICAL STIMULATION

This application claims the benefit of U.S. Provisional Patent Application Ser. No. 61/222,738, filed Jul. 2, 2009, the disclosure of which is incorporated herein by reference.

STATEMENT OF GOVERNMENT SUPPORT

This invention was supported by a grant from the National Institute of Health, Department of Health and Human Services under contract number R43HD062065. The government may have certain rights in this invention.

COPYRIGHT STATEMENT

A portion of the disclosure of this document contains material subject to copyright protection. No objection is made to the facsimile reproduction of the patent document or this disclosure as it appears in the Patent and Trademark Office files or records, but any and all rights in the copyright(s) are otherwise reserved.

TECHNICAL FIELD

The present disclosure relates to the physical therapy arts and, more particularly, to apparatus and methods for providing therapy with electrical stimulation and related methods.

BACKGROUND OF THE INVENTION

Various types of physical therapy, including rehabilitative exercise, may employ externally applied, transcutaneous stimulation in the course of treating a subject. Typically, the stimulation comprises discrete electrical pulses generated by an external stimulator, and travel through associated wires to one or more electrode pairs placed on the skin adjacent a target location. In the case of exercise therapy, the electricity passing through the skin causes the targeted muscle fibers to activate or contract, even without voluntary control by the subject. Accordingly, such stimulation is frequently used in situations where the subject is incapacitated or otherwise unable to control function of the muscles, such as in the event of an injury to the brain or associated portion of the nervous system.

Despite the past use of electrical stimulation for providing therapy, certain limitations in the application of this technology and the results produced remain. For one, a pair of electrodes is typically associated with a single stimulation channel providing the electrical pulses to the targeted location. Thus, to simultaneously or even sequentially provide stimulation to different muscle groups or otherwise in a distributed fashion, pairs of electrodes must each be connected to a different channel of a stimulation source using individual wire for transmitting the pulses. Thus, for example, to stimulate three different muscle groups, three pairs of electrodes would be used, with each pair having an individual wire for transmitting the stimulation pulses from a three channel stimulator (and, to make the wires universal, they are typically made longer than necessary to reach a given body part). Aside from greatly increasing the cost and complexity, such wires may easily become tangled or damaged during the exercise movement.

In typical applications, the stimulation pulses delivered from the source are also infinitesimally small compared to the inter-pulse interval. For example, a given pulse may be active for less than 1,000 milliseconds for every 20,000 milliseconds of time that passes. Thus, there is a substantial amount of unused potential of the stimulation device while it waits to deliver the next pulse.

Accordingly, a need is identified for apparatus and methods that provide an improvement in delivering electrical stimulation to a subject in an efficient and effective manner. In particular, the apparatus would use a single transmission line per channel connected to serially arranged nodes, each associated with an electrode pair, to minimize the number of wires required. This would potentially allow for the application of stimulation to an unprecedented number of channels without significantly adding to the complexity or cost. Moreover, the apparatus would be capable of maximizing the potential of the stimulation device, which further enhances efficiency and reduces cost. Overall, a significant improvement over known past approaches would be realized.

SUMMARY OF THE INVENTION

One aspect of the disclosure is an apparatus for providing electrical stimulation to a subject from a stimulation unit using a transmission line and a plurality of electrodes. The apparatus comprises a plurality of discrete nodes, each adapted to connect to the transmission line for receiving the electrical stimulation and to connect with at least one pair of the plurality of electrodes.

In one embodiment, the nodes are serially connected to the transmission line. Thus, a first node is adapted to be connected to the stimulation unit by a first segment of the transmission line, and further adapted to be connected to a second segment of the transmission line. A second node is adapted to be connected to the second segment of the transmission line, and this succession may be repeated.

A first end of the first segment of the transmission line may be connected to the stimulation unit, and the first node provided with a first receptacle for connecting with a second end of the first segment. The second node includes a first receptacle for connecting with a second end of a second segment. Each node may further include an indicator indicating the provision of stimulation from the unit to the node.

A first node may include a circuit adapted for receiving the stimulation from the stimulation unit. The circuit may be adapted to receive a pulse train of stimulation and output only pulses intended for the corresponding node. Alternatively or additionally, the circuit may be adapted to activate the first node while a second node remains inactive.

The subject may have a plurality of different muscle groups in need of stimulation. In such case, a first node is arranged to stimulate a first of the muscle groups and a second node being arranged to stimulate a second one of the muscle groups. A garment adapted to be worn by the subject may also incorporate the plurality of nodes.

Another aspect of the disclosure relates to an apparatus for providing electrical stimulation from a stimulation unit to a subject using a plurality of electrodes. The apparatus comprises a plurality of nodes for receiving the stimulation associated with a pair of electrodes. Each adjacent node is connected by at least one transmission line. At least a first node of the plurality of nodes comprises a circuit adapted to operate in one of a first mode to allow stimulation pulses to pass to the subject donning the electrodes and a blocking mode to block pulses intended for other nodes. Preferably, the plurality of nodes are connected to each other and the stimulation unit in a daisy chain.

Still another aspect of the disclosure pertains to an improvement in a system for providing neuromuscular electrical stimulation as the result of a stimulation signal provided from stimulation unit to a plurality of pairs of electrodes positioned on a skin surface of a human subject. The improvement comprises at least one node associated with a transmission line and each electrode pair, said node adapted for receiving and processing the stimulation signal from the stimulation unit.

The improvement may further include a plurality of discrete nodes connected to the transmission line in a daisy chain. At least the first node may include a circuit adapted to operate in one of a first mode to receive a pulse train of stimulation from the stimulation unit in which every $i^{th}$ pulse is intended for the $i^{th}$ node, or a second mode to receive a pulse train for activating a selected node to provide the stimulation while another node remains inactive.

The transmission line may comprise a first segment having a first end connected to the stimulation unit and a second end removably connected in a first receptacle on the first node, and further including a second segment having a first end connected in a second receptacle on the first node. The second segment may include a second end for removably connecting with a second receptacle on a second node.

Preferably, the stimulation unit includes a first output channel for connecting with the plurality of discrete nodes and further including a second output channel for connecting with a second plurality of discrete nodes. Each node in the second plurality of discrete nodes may be associated with at least two electrodes.

Yet another aspect of the disclosure relates to an apparatus for providing electrical stimulation to a subject using a plurality of electrodes. The apparatus comprises a plurality of nodes, each node adapted to connect to at least one pair of the plurality of electrodes and provide stimulation to the subject using the electrodes, and a stimulation unit for providing a first train of stimulation pulses in which every $i^{th}$ pulse is intended for the $i^{th}$ node.

Preferably, the nodes are connected by a single transmission line in a daisy chain. Besides the first train, the stimulation unit may be adapted for providing a second train of stimulation pulses in which every pulse is intended for a selected node. Each node may include a pulse gating circuit adapted to output a selected pulse from the first train of stimulation pulses.

A further aspect of the disclosure pertains to a kit for forming an apparatus for providing electrical stimulation to a subject from a stimulation unit using a transmission line and a plurality of electrodes. The kit comprises a plurality of nodes, each including at least one receptacle adapted to connect to the transmission line, and a plurality of electrode pairs, each for connecting to one of the plurality of nodes. A related aspect comprises a computer-implemented method for providing stimulation for a subject using a stimulation unit, including programming the stimulation unit to operate in combination with the kit.

Related methods disclosed include a method for forming an apparatus for providing electrical stimulation to a subject from a stimulation unit using a first transmission line and a plurality of electrodes. The method comprises connecting a plurality of discrete nodes to the first transmission line, each node adapted for connecting to at least one pair of electrodes. The connecting step may comprise positioning a first removable connector of the transmission line in a first receptacle of a first node. The connecting step may further comprise connecting a second removable connector of the transmission line in a second receptacle of a first node; and connecting a third removable connector of the transmission line in a first receptacle of a second node. The method may further include the step of providing the nodes on a garment. The step of programming the stimulation unit to provide a pulse train in which every $i^{th}$ pulse is intended for the $i^{th}$ node may also form part of the method, as may the step of programming the stimulation unit to provide a pulse train in which a group of sequential pulses are intended for a selected node.

The disclosure also relates to a method for providing electrical stimulation to a subject using a plurality of electrodes. The method comprises providing a plurality of nodes, each node adapted to connect to at least one pair of the plurality of electrodes, and providing a first train of stimulation pulses in which every $i^{th}$ pulse is intended for the $i^{th}$ node. The method may further include the step of providing a second train of stimulation pulses in which every pulse is intended for a selected node.

DETAILED DESCRIPTION OF THE INVENTION

One embodiment relates to an active distributed electrode array (ADEA) system 10 for electrical stimulation therapy and, neuromuscular electrical stimulation, in particular. The system 10 includes a stimulation unit 12 having at least one output that, using other components described herein, may be shared to provide essentially an unlimited number of virtual stimulation channels with intelligently controlled coordinated simulation patterns. This allows for use in high channel count applications without the added cost and complexity of a rigidly defined high channel count NMES unit. The system 10 further allows virtual stimulation channels to be added and/or removed as needed by the therapist to form a low-cost network of stimulation nodes using a minimal set of wires and simulation that is controlled automatically by the stimulation unit 12.

Figure 1:
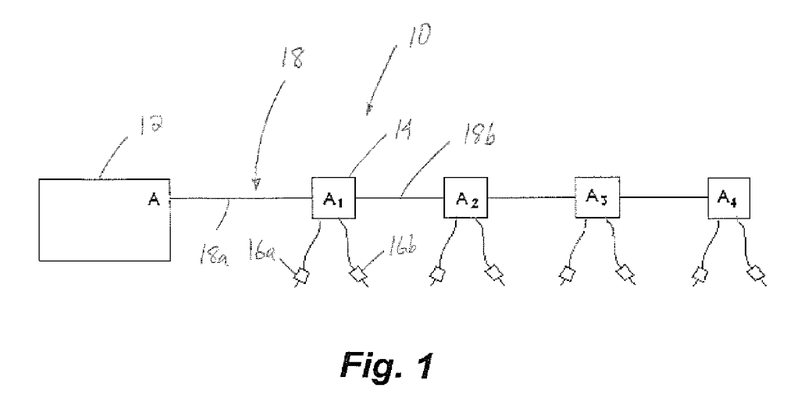
FIG. 1 is a schematic diagram illustrating one embodiment of a stimulation system in accordance with the principles disclosed herein.

As shown in FIG. 1, the stimulation unit 12 is adapted to output stimulation pulses to at least one, and preferably a plurality of discrete stimulation nodes 14 (i.e., virtual channels) associated with each output channel, rather than to a single electrode pair. Each node 14, is in turn, associated with a pair of electrodes 16a, 16b, for applying the stimulation to a particular location, such as the skin surface adjacent a muscle or muscle group of a human subject in need of therapy (e.g., assisted exercise or rehabilitation, including possibly pain management). As illustrated, these electrodes 16a, 16b may be discrete and thus comprise separate flat pads of a flexible material, and may be associated with suitable fasteners (adhesives, straps, bands, etc., not shown) for attachment to the skin surface. Four nodes 14 are shown in FIG. 1 for purposes of illustration, but is should be appreciated that any number could be used. In the illustrated embodiment, the node 14 is connected to a surface of the electrode pad opposite the surface for applying the stimulation to the skin surface of the subject, but it should be appreciated that the node could be a separate structure as well.

Figures 2, 2A:
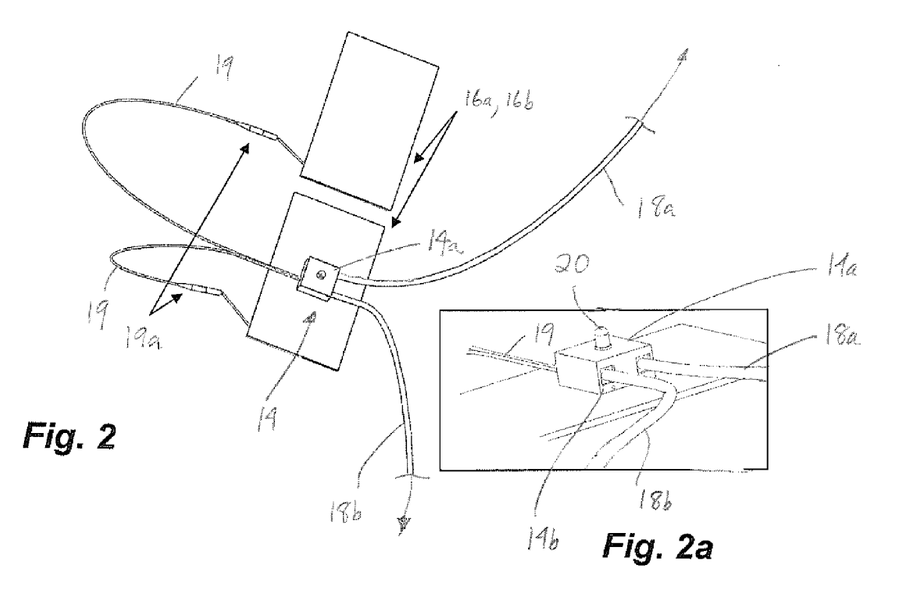
FIG. 2 illustrates a single stimulation node according to one aspect of the disclosure.
FIG. 2a is a close-up view of the stimulation node of FIG. 2.

The nodes 14 may be connected together and to the stimulation unit 12 using suitable a transmission line 18, which may comprise multiple wires and thus be adapted to provide not only the simulation pulses, but also communication signals. Preferably, the connection is made in a daisy-chain fashion, such that a single transmission line 18 connects the stimulation unit 12 to each successive node 14 in the chain. Thus, for example, FIG. 2 shows that the line 18 includes a first segment 18a for connecting the node 14 with the stimulation unit 12, and a second segment 18b for connecting to the next successive node (e.g., A2, if node 14 in FIG. 2 is A1).

As should be appreciated, segments of transmission line 18 may be added for connecting additional nodes 14 to the array. Regardless of the number of segments or precise form used, the use of a single, external transmission line 18 from the stimulation unit 12 to the nodes 14 associated with a particular channel is advantageous because the number of wires that must be managed is greatly reduced (usually, two per channel). This not only greatly simplifies the set up process, but also reduces the potential for damage as the result of the exercise movement.

Figure 3:
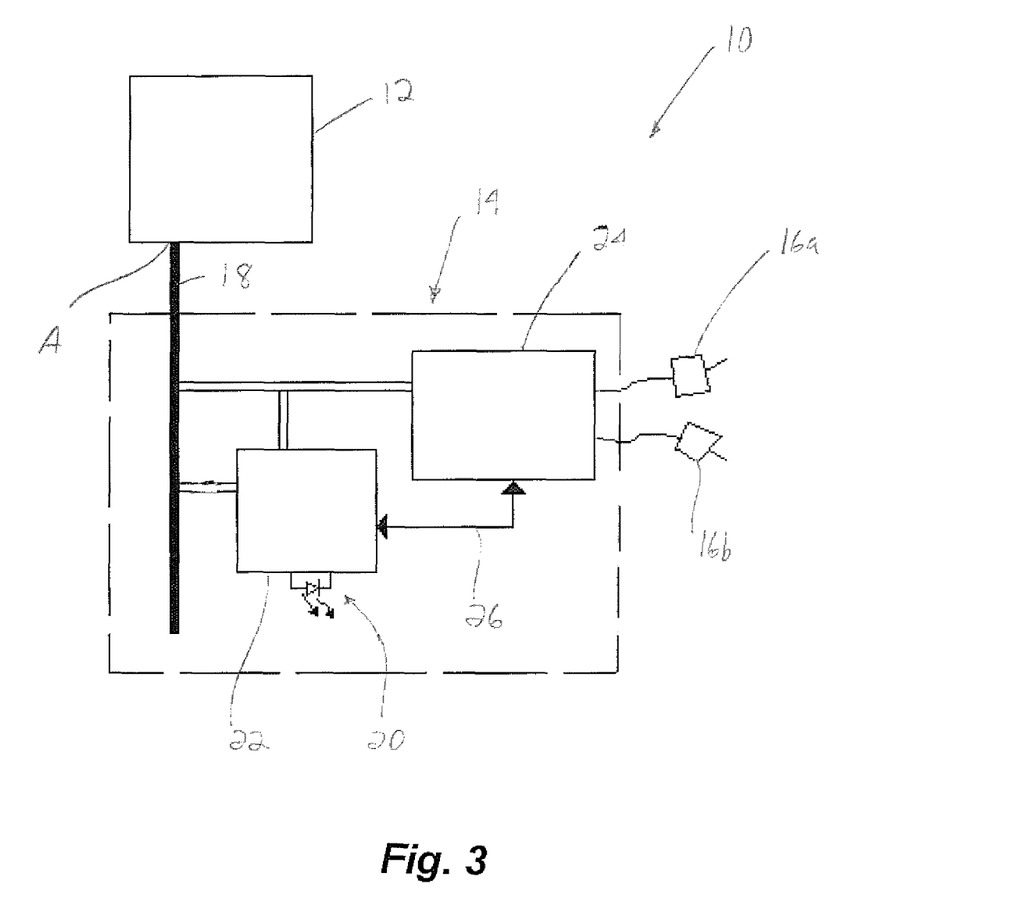
FIG. 3 is a schematic diagram illustrating the details of a circuit included in one or more of the stimulation nodes.

Referring to the block diagram in FIG. 3, the node 14 is shown as being connected to a simulation unit 12 via a port A (which as should be appreciated corresponds to virtual channels A1-A4 in the illustrated embodiments). This port A may provide the nodes 14 with power, communication, and access to the stimulation output channel of the unit 12. Preferably, there are two stimulation channels delivered through different ports A and B to distinct arrays of discrete nodes 14 arranged in tandem (see FIGS. 7 and 8), but more or fewer may be used depending on the particular application.

The connection of the segments 18a, 18b to the node 14 is made in a releasable fashion. For example, in the illustrated embodiment, the node 14 comprises a housing 14a (which is optional), and releasability is achieved using suitable receptacles 14b on the housing 14a. These receptacles 14b may take the form of a conventional telephone (RJ-11) jack, for associating with suitable connectors on the corresponding ends of the segments 18a, 18b. By using common connectors releasably attached in this manner, the nodes 14 may be added or removed along the transmission line 18 with ease.

Suitable lines 19 also connect each node 14 to the electrodes 16a, 16b for providing the stimulation pulses. This connection may also be established using releasable connectors 19a (e.g., pins for positioning in jacks associated with pigtail leads) to allow for the removal and replacement of the electrodes 16a, 16b, if necessary or desired. The node 14 is shown in FIGS. 2 and 2a as being carried by one of the electrodes 16a, 16b in the pair, but this is entirely optional. Each node 14 may also associate with an indicator 20 for providing a signal indicating an active condition (i.e., the stimulation current is reaching the node and/or flowing to the electrodes 16a, 16b), as well as possibly indicating the stimulation intensity (e.g., as a function of current).

At least one, and preferably all of the nodes 14 are "intelligent" and thus may be adapted to receive and process the stimulation pulses received from the stimulation unit 12. For example, the nodes 14 may process and selectively output the stimulation pulses intended only for an electrode pair 16a, 16b for a particular operation (e.g., stimulating a muscle group), while blocking pulses intended for the other electrodes/muscle groups. To achieve this goal, each node 14 may include a pulse selection circuit 22 and a pulse gating circuit 24, which work together to provide certain predetermined operating modes.

The pulse gating circuit 24 serves as the interface between the stimulation unit 12 and the electrodes 16a, 16b connected to each node 14. In a pass-through mode, the gating circuit 24 allows stimulation pulses from the unit 12 to pass to the subject donning the electrodes when certain amplitude and width specifications are met. In blocking mode, the gating circuit 24 blocks pulses intended for other nodes 14.

The pulse selection circuit 22 in turn is responsible for communicating with the stimulator 12, monitoring the stimulation pulse train on a pulse-by-pulse basis, enabling the pulse gating circuit (such as via an enable line 26), indicating node activity (such as via the stimulation indicator 20, which is shown in FIG. 3 as comprising a light-emitting diode), and allowing for the selection of a particular virtual channel via a selector switch (not shown). A suitable controller associated with each node 14 may be used to perform these functions, or alternatively an application specific integrated circuit (ASIC) may be used.

Figure 4:
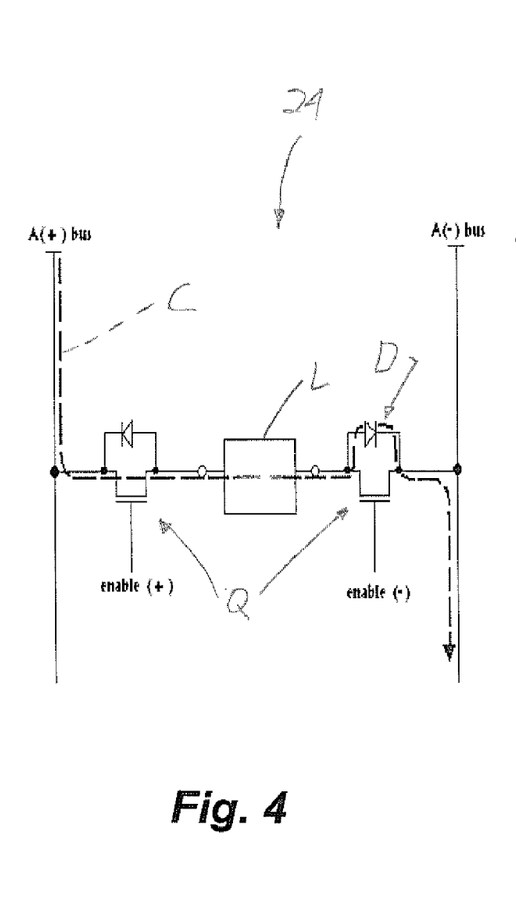
FIGS. 4 and 5 are circuit diagrams showing alternate approaches to a pulse gating circuit that may form part of a stimulation node.
Figure 5:
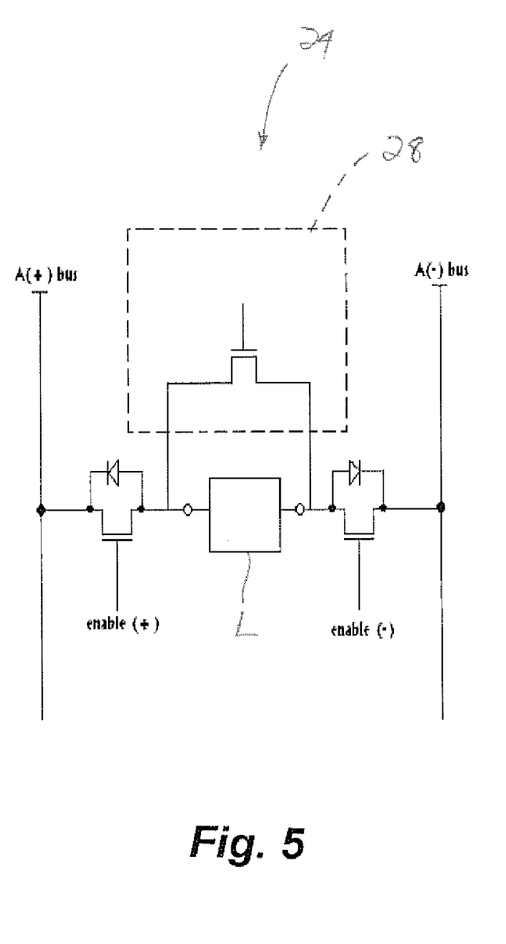

The pulse gating circuit 24 may comprise a discrete transistor-based circuit or a TRIAC, but other arrangements may be possible as well. For example, FIGS. 4 and 5 present schematic diagram for two possible alternative applications for forming the pulse gating circuit 24 for each stimulation node 14 of the system 10. The block L represents the load (i.e., the electrodes 16a, 16b connected by tissue), and transistors Q control current flow through the load L when the stimulation unit 12 generates a pulse on the "A" stimulation bus. Current flow (shown as dashed line C in this example) proceeds from the A(+) stimulation output through the transistor Q, load L, and diode D before returning to the unit 12 via the A (−) bus. This flow may be reversed to pass the second phase when two events occur: (1) the pulse selection circuit 22 withdraws the enable (+) line and asserts the enable (−) line, and (2) the stimulator 12 switches the polarity of the A(+) and A(−) bus in preparation for generating the second phase of the stimulation pulse.

In FIG. 5, the shunt circuit 28 comprises an extra transistor that is placed in parallel with the electrodes (i.e., load L). This circuit 28 is intended to prevent an unintended muscle contraction caused by leakage current through the gating circuit 24 (i.e., a pulse that is not fully blocked when the gating circuit is disabled). This provides a path for the leakage current to flow that bypasses the electrodes. The transistor of shunt circuit 26 would be enabled whenever both legs of the gating circuit 24 are disabled. Alternatively, two relays (not shown) could be used in place of transistors Q in FIG. 4. The relay coil would be excited by the pulse selection circuit 22.

Figure 6:
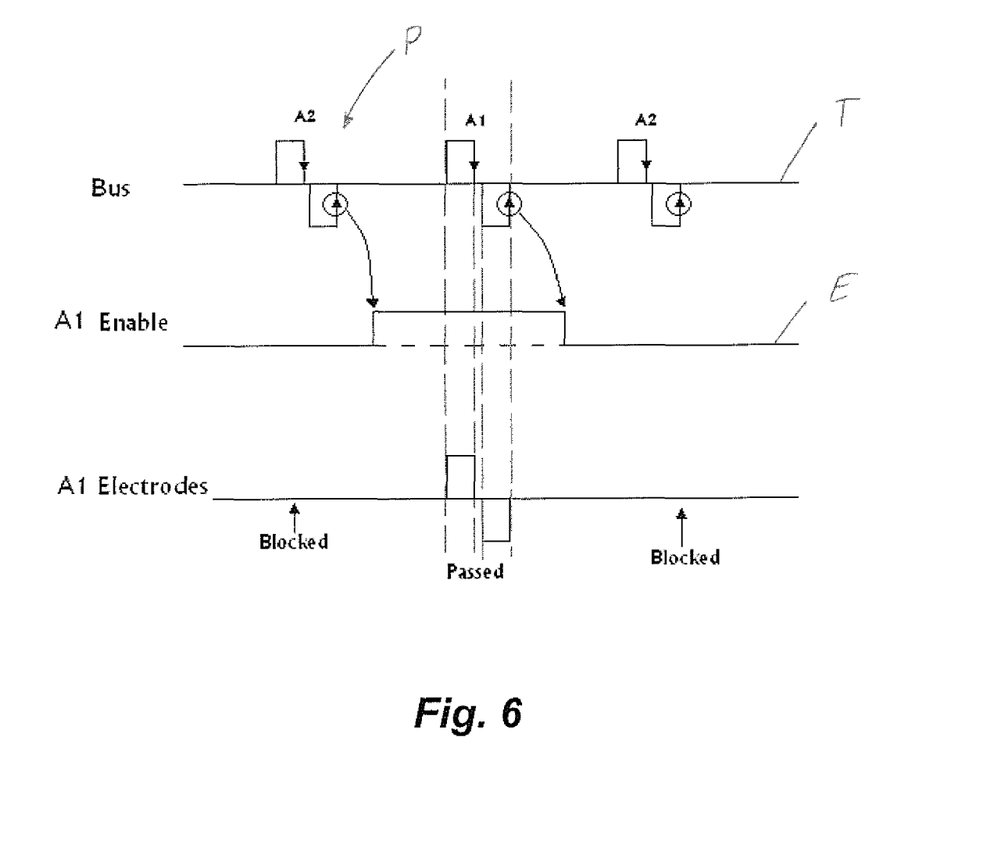
FIG. 6 is a timing diagram showing the possible operation of the pulse gating circuit to control the delivery of stimulation pulses to the electrodes associated with particular nodes.

A timing diagram illustrating one possible embodiment of the monitoring and triggering tasks of the pulse selection circuit 22 is shown in FIG. 6. Pulses P of the interlaced pulse train T are shown for virtual channels A1 and A2. Trigger events are shown on the falling edges of each stimulation pulse P, and may cause a microcontroller interrupt, such that the interrupt service routine determines if the output of the pulse gate circuit 24 of a particular node 14 should be enabled (such as by counting the pulses and enabling for pulses which are intended to be output using the particular electrodes 16a, 16b). To enable a pulse P to the particular virtual channel, the enable signal E may be set high during the inter-pulse interval before the pulse to be output and return to the disabled state during the inter-pulse interval following the desired pulse output. The output to the A1 electrodes 16a, 16b are shown, indicating that the A1 pulse passes and the A2 pulses are blocked.

Alternative arrangements may also be used to control the gating circuit 24. For instance, a microcontroller associated with each node 14 could use an error-checking scheme to determine the inter-phase interval (i.e., the period between anodic and cathodic pulses for the same channel) from the inter-pulse interval (i.e., the period between successive pulses for different channels), and then disable the node if an error is detected. Alternative approaches could be the use of pulse width to evaluate which pulses should be outputted using the electrodes associated with a node 14, or an asynchronous clocking scheme in which the nodes and stimulation unit 12 employ synchronized clock rates to output pulses during a particular window of time. Yet another alternative approach could be for the controller (stimulation unit 12) to send a command during the interpulse interval to enable the desired channel prior to outputting a pulse.

Figure 7:
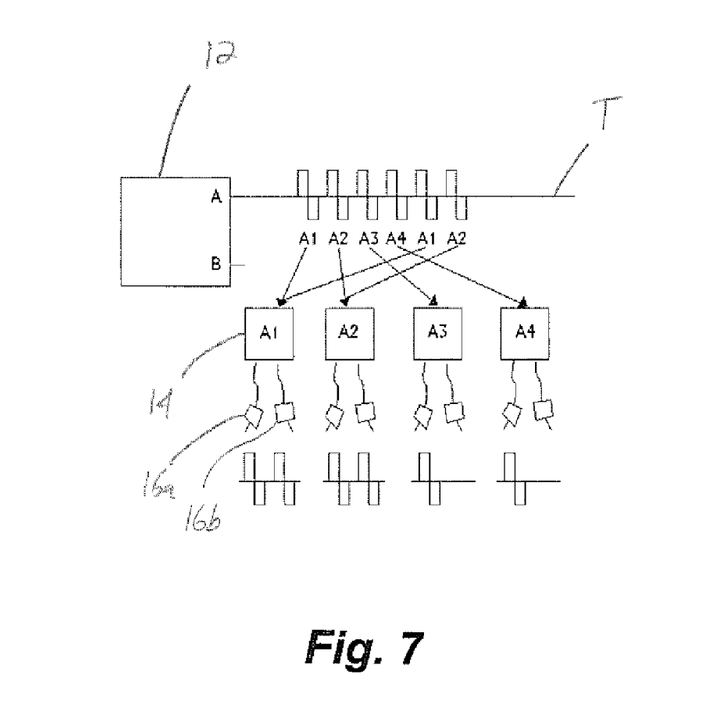
FIGS. 7 and 8 illustrate two different modes of operation of the system.
Figure 8:
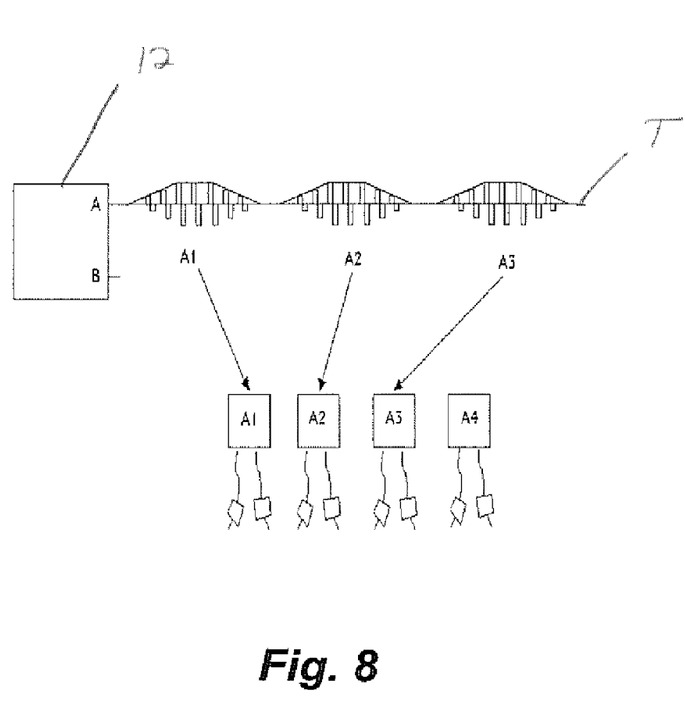

In any case, the system 10 may be configured to operate in two possible modes: (i) pulse sharing; and (ii) channel phasing. In pulse sharing mode, the unit will configure a plurality of virtual channels (e.g., A1-A4) to be active and then output an interlaced pulse train T of stimulation provided by stimulation unit 12 in which every $i^{th}$ pulse is intended for the $i^{th}$ node 14. Thus, as shown in FIG. 7, the nodes 14 will parse the pulse train T to selectively output only the pulses intended for the particular node 14 (i.e., output every $4^{th}$ pulse). In this mode, the stimulation unit 12 may be used to simultaneously activate multiple muscle groups using a single channel and thus form a distributed array.

In channel phasing mode, the unit 10 may activate a selected virtual channel (A1, A2, or A3) while other channels (e.g., A4) are inactive. The unit 12 may then be used to output a traditional stimulation pulse train T. The pulses are delivered by only the electrodes 16a, 16b associated with the active virtual channel. This mode of operation is shown schematically in FIG. 8. These modes may be used in combination such that the stimulation unit 12 essentially has an unlimited number of channels for a given transmission line 18.

Figure 9:
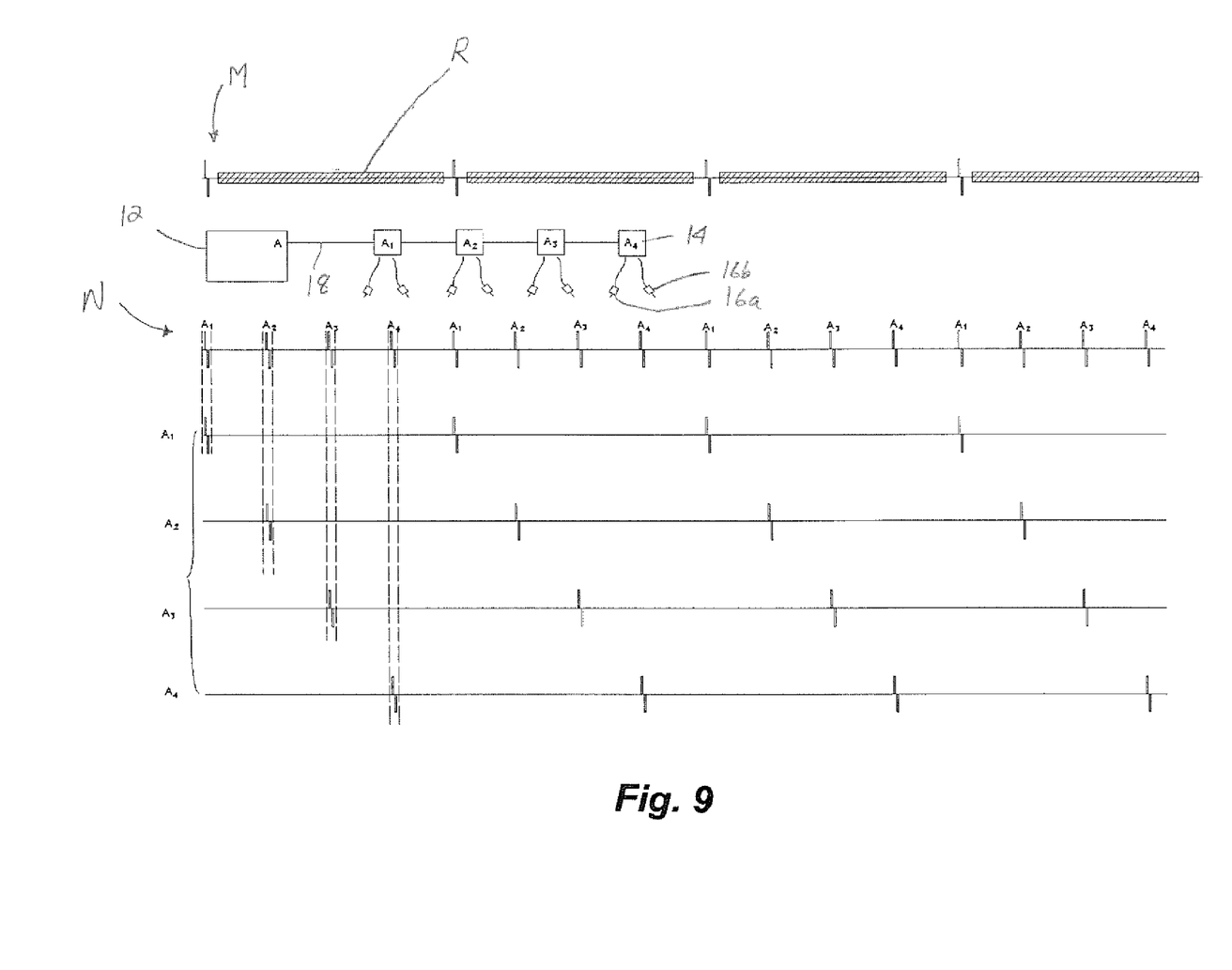
FIG. 9 is a diagram illustrating the nature of the improvement in efficiency that may be achieved using the disclosed system.

As can be best understood with reference to FIG. 9, use of these aspects of the system 10 together (which is optional) may provide several advantages. At the top of this figure, a traditional electrical stimulation pulse train M to a single electrode pair is shown. Stimulation pulses are infinitesimally small compared to the inter-pulse interval (e.g., less than or equal to 1000 ms active per every period greater than or equal to 20,000 ms). The shaded region R indicates the unused potential of the stimulation device as it waits to deliver the next pulse. With the present system 10, the stimulation unit 10 may output the interlaced pulse train N as shown, which includes pulses for virtual channels A1-A4. All connected stimulation nodes 14 receive the interlaced pulse train N and either output the pulses to the connected electrode pair 16a, 16b or block pulses intended for other nodes/virtual channels.

Figure 10:
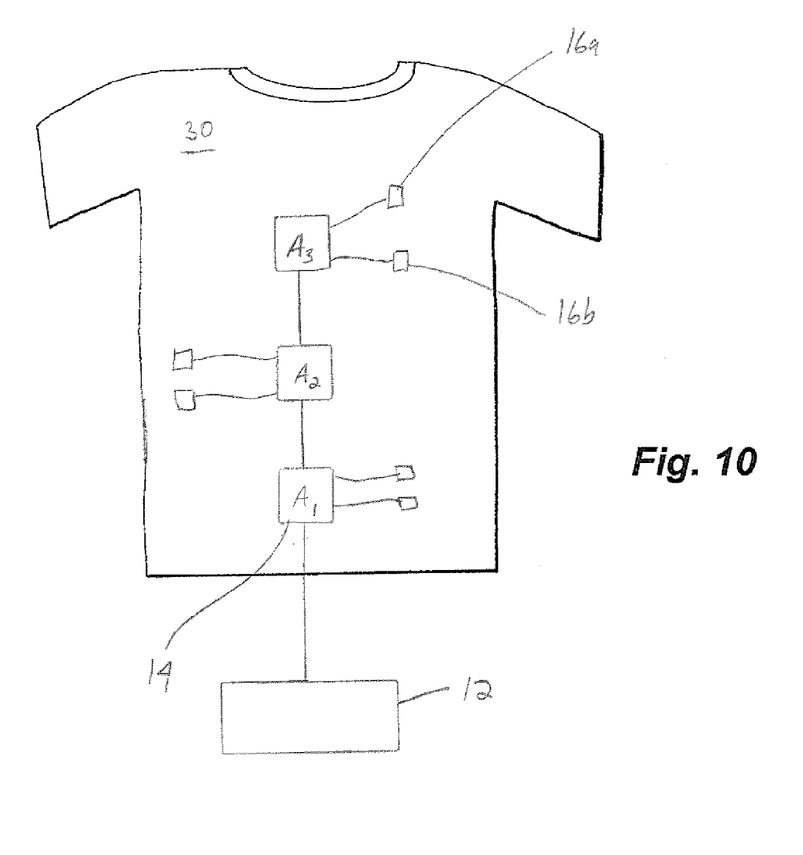
FIG. 10 is a schematic diagram of a stimulation garment that may be used in connection with the disclosed system.

The modular nature of the system 10 allows for selected components to be provided as a kit. For example, the kit may comprise a plurality of nodes 14 and electrode pairs 16a, 16b, both adapted for connecting to the associated transmission line 18, 19. The kit may be provided for use by product developers for use in a particular stimulation application. The components of the system 10 or the kit could also be incorporated into a stimulation garment 30 (shown as a shirt in FIG. 10 as one example, but the garment may also comprise a sleeve, band, pant, or the like, depending on the particular need of the subject).

Figure 11:
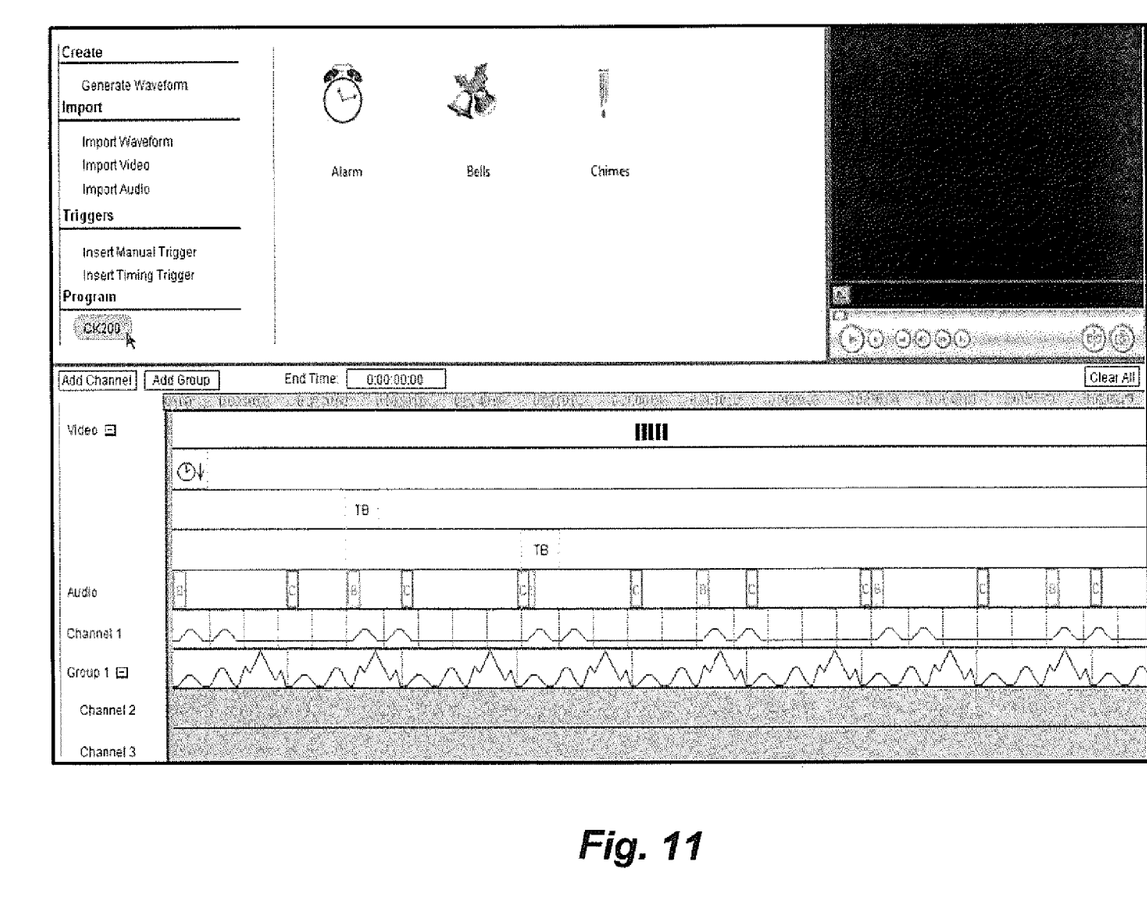
FIGS. 11-13 comprise screen shots from software programs that may be used for programming the system.
Figure 12:
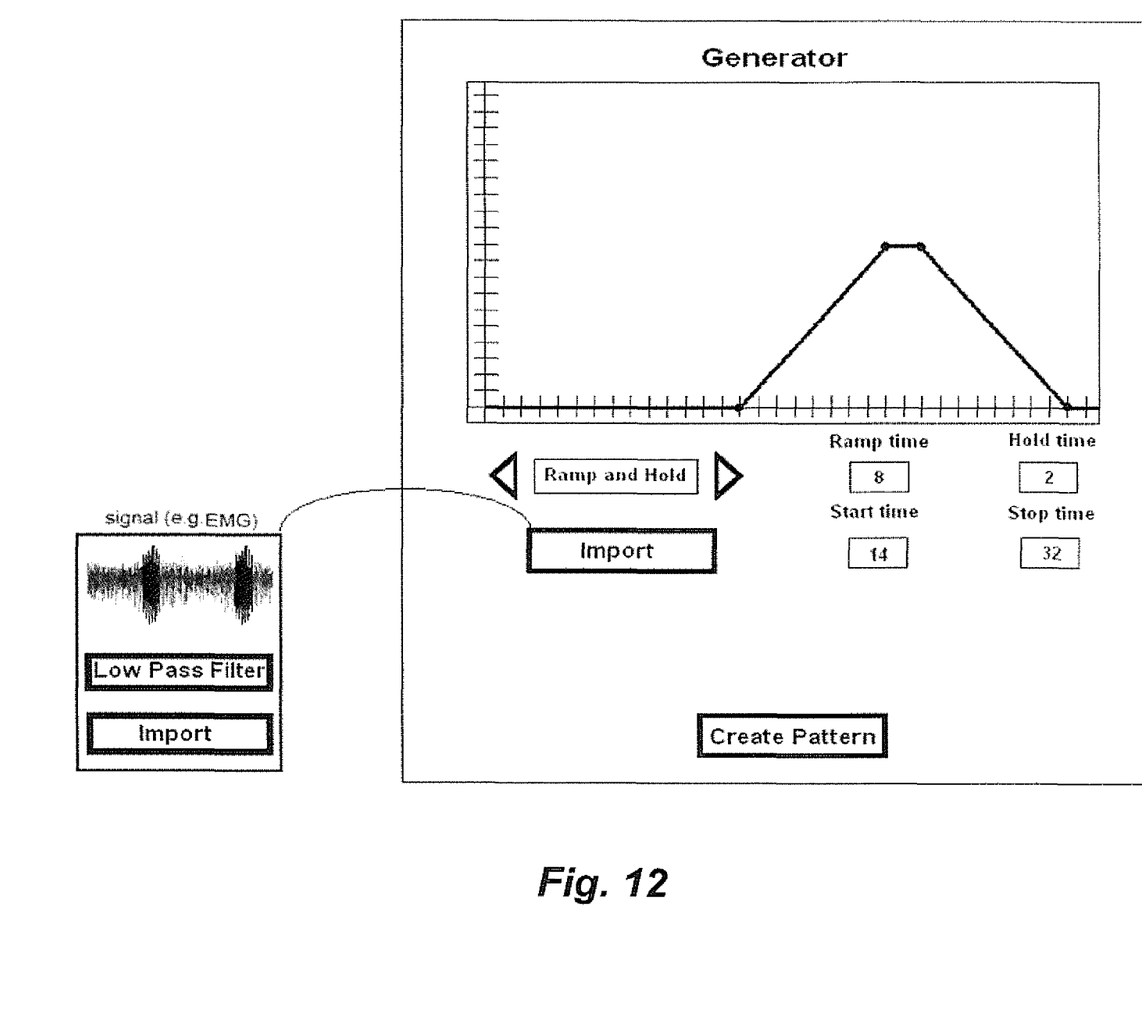
Figure 13:
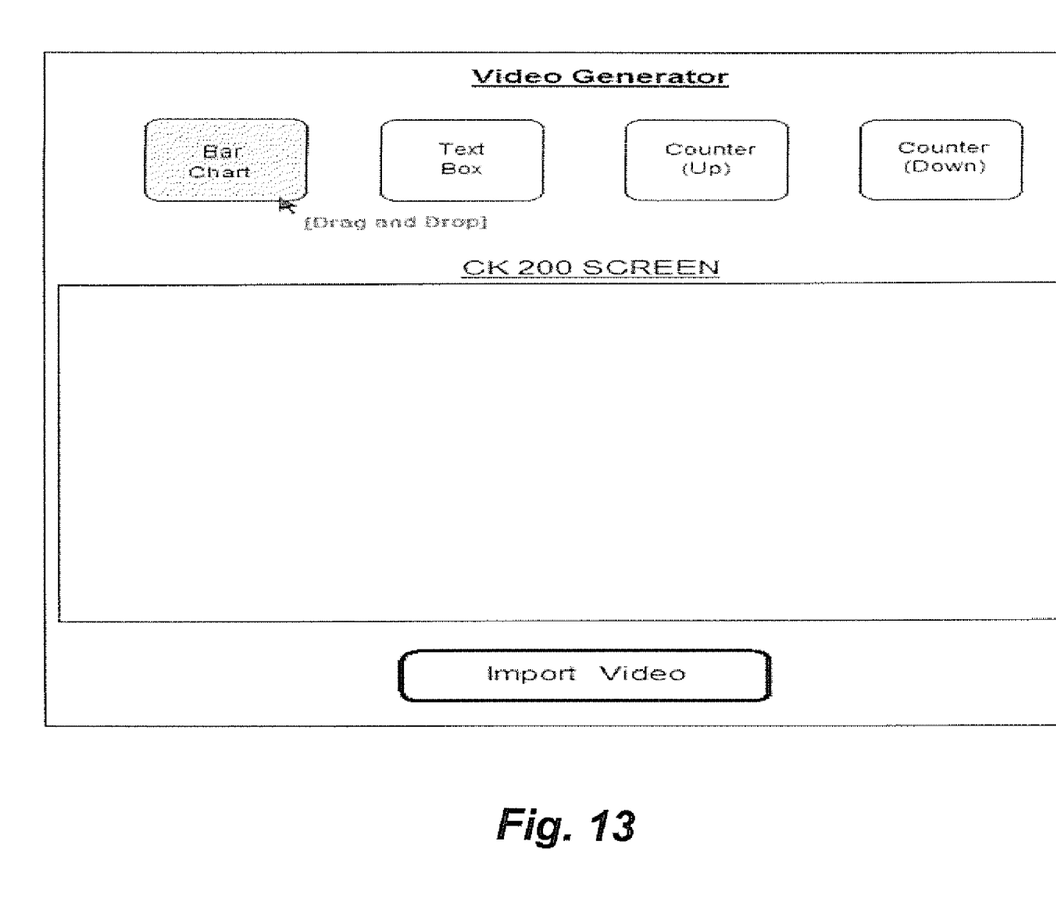

The stimulation unit 12 may be programmed to provide the stimulation patterns desired for each electrode or group of electrodes to meet the individual needs of the patient. This programming may be done, for example, by using a software application for designing a particular stimulation regimen, including the ability to program the different virtual channels simultaneously (see FIG. 11, a screen shot from an application for designing stimulation regimens; FIG. 12, which is a pattern generator application; and FIG. 13, which is a program for designing the display output on a stimulation unit 12). Alternatively or additionally, pre-programmed stimulation paradigms may be provided, and at power-up the stimulation unit 12 may evaluate the connected nodes 14 and automatically bypass those not in use. In this case, the array size would be easily scalable by the end user (a physical therapist or even a patient) by simply adding or removing nodes 14 to the particular stimulation channel(s).

As should also be appreciated, the modular nature of the nodes 14 allows for their positioning in a stimulation array that may be distributed among several different muscle groups. For example, different nodes 14 may be associated with the subject's quadriceps, gluteals, and hamstrings. In this manner, a complete stimulation solution may be provided using a single stimulation channel. The nodes 14 need not be limited to a particular body part or region of the body, but may extend over multiple body parts (e.g., the chest, shoulder, and arm; the back or abdomen and legs, etc.).

To further facilitate the portability of the system 10 and concomitant ease of use, the stimulation unit 12 preferably comprises a portable, hand-held battery operated device. For example, the unit 12 may take the form of the CK200 device available from customKYnetics, Inc. of Versailles, Ky. Certain features of this unit 12 are described in U.S. patent application Ser. Nos. 12/164,554 and 60/937,633, the disclosures of which are incorporated herein by reference.

The foregoing descriptions of various embodiments of the invention are provided for purposes of illustration and not intended to be exhaustive or limiting. Modifications or variations are also possible in light of the above teachings. The embodiments described above were chosen to provide the best application to thereby enable one of ordinary skill in the art to utilize the disclosed inventions in various embodiments and with various modifications as are suited to the particular use contemplated. All such modifications and variations are within the scope of the invention.

The invention claimed is:

1. An apparatus for providing electrical stimulation to a subject from a stimulation unit including a port for connecting to a first end of a single transmission line external to the stimulation unit and a plurality of electrodes for delivering the stimulation to an external skin surface of the subject, comprising:
   a plurality of discrete nodes, each adapted to connect to the transmission line for receiving the electrical stimulation, and each adapted to connect with at least one pair of the plurality of electrodes to supply the electrical stimulation to the electrodes for delivery to the external skin surface;
   wherein the plurality of discrete nodes are each external to the stimulation unit.

2. The apparatus of claim 1, wherein a first node is adapted to be connected to the stimulation unit by a first segment of the transmission line.

3. The apparatus of claim 2, wherein the first node is adapted to be connected to a second segment of the transmission line, and a second node is adapted to be connected to the second segment of the transmission line.

4. The apparatus of claim 3, wherein a first end of the first segment is connected to the stimulation unit, and the first node includes a first receptacle for connecting with a second end of the first segment.

5. The apparatus of claim 4, wherein the second node includes a first receptacle for connecting with a second end of a second segment.

6. The apparatus of claim 1, wherein each node includes an indicator indicating the provision of stimulation from the unit to the node.

7. The apparatus of claim 1, wherein a first node includes a circuit adapted for receiving the stimulation from the stimulation unit.

8. The apparatus of claim 7, wherein the circuit is adapted to receive a pulse train of stimulation and output only pulses intended for the corresponding node.

9. The apparatus of claim 7, wherein the circuit is adapted to activate the first node while a second node remains inactive.

10. The apparatus of claim 1, wherein the subject has a plurality of different muscle groups in need of stimulation, a first node being arranged to stimulate a first muscle group and a second node being arranged to stimulate a second muscle group.

11. A garment including the apparatus of claim 1 and adapted to be worn by the subject.

12. The apparatus of claim 1, wherein each node includes at least one connector for releasably connecting to the transmission line.

13. The apparatus of claim 1, wherein each of the nodes is positioned between the transmission line and at least one pair of electrodes.

14. The apparatus of claim 1, wherein at least one node includes a housing.

15. The apparatus of claim 14, wherein the housing includes at least two connectors, each adapted for connecting to a segment of the transmission line.

16. The apparatus of claim 1, wherein at least one node further includes first and second connectors, and wherein the first connector is adapted to connect to a first segment of the transmission line for receiving input from the stimulation unit and the second connector is adapted to connect to a second segment of the transmission line for transmitting input to a different node.

17. An apparatus for providing electrical stimulation from a stimulation unit to a subject using a plurality of electrodes, comprising:
a plurality of nodes for receiving the stimulation associated with a pair of electrodes, each node connected to at least one adjacent node by at least one transmission line, wherein at least a first node of said plurality of nodes comprises a circuit adapted to operate in one of a first mode to allow stimulation pulses to pass to the subject donning the electrodes and a blocking mode to block pulses intended for other nodes.

18. The apparatus of claim 17, wherein the plurality of nodes are connected to each other and the stimulation unit in a daisy chain.

19. In a system for providing electrical stimulation as the result of a stimulation signal provided from stimulation unit to a plurality of pairs of electrodes positioned on an external skin surface of a human subject, the improvement comprising at least one node external to the stimulation unit, said node associated with a transmission line and each electrode pair, said node adapted for receiving and processing the stimulation signal from the stimulation unit.

20. The improvement to the system according to claim 19, further including a plurality of discrete nodes connected to the transmission line in a daisy chain.

21. The improvement to the system according to claim 20, wherein at least the first node includes a circuit adapted to operate in one of a first mode to receive a pulse train of stimulation from the stimulation unit in which every ith pulse is intended for the ith node, or a second mode to receive a pulse train for activating a selected node to provide the stimulation while another node remains inactive.

22. The improvement to the system of claim 20, wherein the transmission line comprises a first segment having a first end connected to the stimulation unit and a second end removably connected in a first receptacle on the first node, and further including a second segment having a first end connected in a second receptacle on the first node.

23. The improvement to the system of claim 20, wherein the second segment includes a second end for removably connecting with a second receptacle on a second node.

24. The improvement to the system of claim 20, wherein the stimulation unit includes a first output channel for connecting with the plurality of discrete nodes and further including a second output channel for connecting with a second plurality of discrete nodes, each node in the second plurality of discrete nodes associated with at least two electrodes.

25. An apparatus for providing electrical stimulation to a subject using a plurality of electrodes, comprising:
a plurality of nodes, each node adapted to connect to at least one pair of the plurality of electrodes and provide stimulation to the subject using the electrodes; and
a stimulation unit for providing a first train of stimulation pulses in which every ith pulse is intended for the ith node.

26. The apparatus of claim 25, wherein the nodes are connected by a single transmission line in a daisy chain.

27. The apparatus of claim 25, wherein the stimulation unit is adapted for providing a second train of stimulation pulses in which every pulse is intended for a selected node.

28. The apparatus of claim 25, wherein a first node includes a pulse gating circuit adapted to output a selected pulse from the first train of stimulation pulses.

29. The apparatus of claim 25, wherein at least the $i^{th}$ node further includes a circuit adapted to selectively allow the $i^{th}$ pulse to pass to the subject via the electrodes and to allow an $(i+n)^{th}$ pulse to pass from the $i^{th}$ node to an $(i+n)^{th}$ node.

30. A kit for forming an apparatus for providing electrical stimulation to a subject from a stimulation unit using a transmission line, comprising:
a plurality of nodes, each including at least one receptacle adapted to releasably connect to the transmission line; and
a plurality of electrode pairs, each for connecting to one of the plurality of nodes.

31. A computer-implemented method for providing stimulation for a subject using a stimulation unit, comprising programming the stimulation unit to operate in combination with the kit of claim 30.

32. A method for forming an apparatus for providing electrical stimulation to a subject from a stimulation unit using a first transmission line and a plurality of electrodes, comprising:
connecting a plurality of discrete nodes to the first transmission line, each node adapted for connecting to at least one pair of electrodes.

33. The method of claim 32, wherein the connecting step comprises positioning a first removable connector of the transmission line in a first receptacle of a first node.

34. The method of claim 32, wherein the connecting step further comprises:
releasably connecting a second connector of the transmission line in a second receptacle of a first node; and
releasably connecting a third connector of the transmission line in a first receptacle of a second node.

35. The method of claim 34, further including the step of providing the nodes on a garment adapted to be worn by the subject.

36. The method of claim 34, further including the step of programming the stimulation unit to provide a pulse train in which every ith pulse is intended for the ith node.

37. The method of claim 34, further including the step of programming the stimulation unit to provide a pulse train in which a group of sequential pulses are intended for a selected node.

38. A method for providing electrical stimulation to a subject using a plurality of electrodes, comprising:
providing a plurality of nodes, each node adapted to connect to at least one pair of the plurality of electrodes; and
providing a first train of stimulation pulses in which every ith pulse is intended for the ith node.

39. The method of claim 38, further including the step of providing a second train of stimulation pulses in which every pulse is intended for a selected node.

* * * * *